United States Patent
Shah

(10) Patent No.: US 10,183,111 B2
(45) Date of Patent: Jan. 22, 2019

(54) NEEDLE SYSTEM FOR MEDICAL USE

(71) Applicant: Amit Shah, New York, NY (US)

(72) Inventor: Amit Shah, New York, NY (US)

( * ) Notice: Subject to any disclaimer, the term of this patent is extended or adjusted under 35 U.S.C. 154(b) by 149 days.

(21) Appl. No.: 15/066,560

(22) Filed: Mar. 10, 2016

(65) Prior Publication Data

US 2016/0263303 A1 Sep. 15, 2016

Related U.S. Application Data

(60) Provisional application No. 62/131,488, filed on Mar. 11, 2015.

(51) Int. Cl.
*A61M 1/30* (2006.01)
*A61M 1/36* (2006.01)

(52) U.S. Cl.
CPC .......... *A61M 1/3661* (2014.02); *A61M 1/301* (2014.02)

(58) Field of Classification Search
CPC ... A61M 1/3661; A61M 1/301; A61M 1/3659
See application file for complete search history.

(56) References Cited

U.S. PATENT DOCUMENTS

| 8,029,471 B1 * | 10/2011 | Khan-Sahibzada ......................... A61M 1/3653 604/164.01 |
| 2006/0189922 A1 * | 8/2006 | Amarasinghe .... A61M 25/0026 604/28 |

OTHER PUBLICATIONS

Vanholder et al., "Adequacy studies of fistula single-needle dialysis", American journal of Kidney Diseases, vol. X, No. 6, Dec. 1987, pp. 417-426.
National Kidney Foundation. KDOQI Clinical Practice Guidelines and Clinical Practice Recommendations for 2006 Updates: Hemodialysis Adequacy, Peritoneal Dialysis Adequacy and Vascular Access. Am J Kidney Dis 48: S1-S322, 2006 (suppl 1), 183 pages.
Brouwer, Deborah J., "Cannulation Camp: Basic Needle Cannulation Training for Dialysis Staff", Dialysis & Transplantation, vol. 24, No. 11, 1995, 7 pages.

* cited by examiner

*Primary Examiner* — Laura A Bouchelle
*Assistant Examiner* — Tasnim Mehjabin Ahmed
(74) *Attorney, Agent, or Firm* — Hamre, Schumann, Mueller & Larson, P.C.

(57) ABSTRACT

A needle system and methods for using the needle system are described. The needle system is generally intended for medical use and can be used when performing a dialysis on a patient, for example, hemodialysis. In general, the needle system can address problems that commonly arise when using conventional single or double needle systems during hemodialysis.

8 Claims, 6 Drawing Sheets

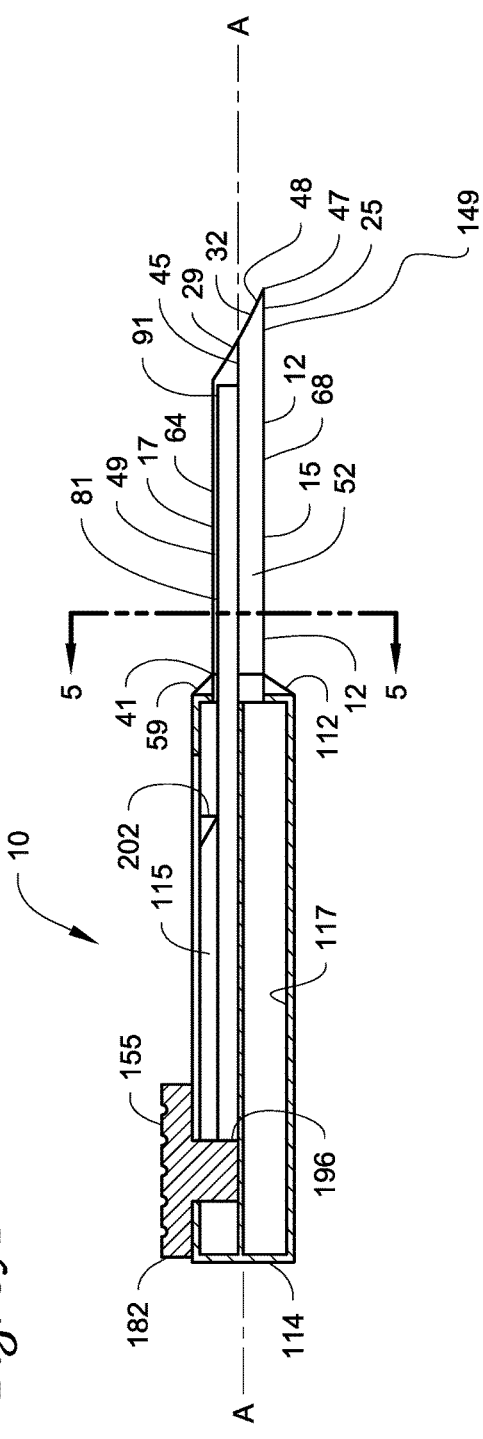
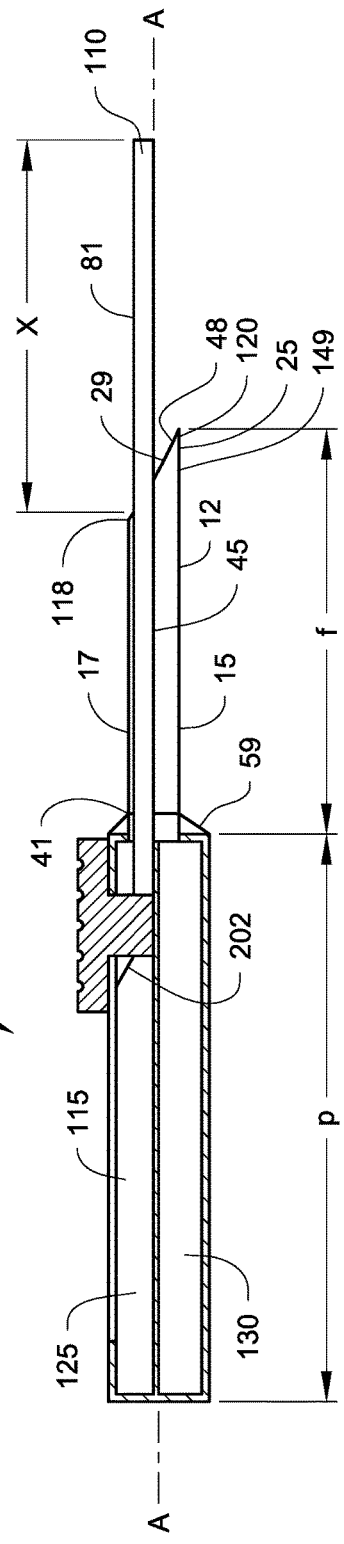
Fig. 3A
Fig. 3B

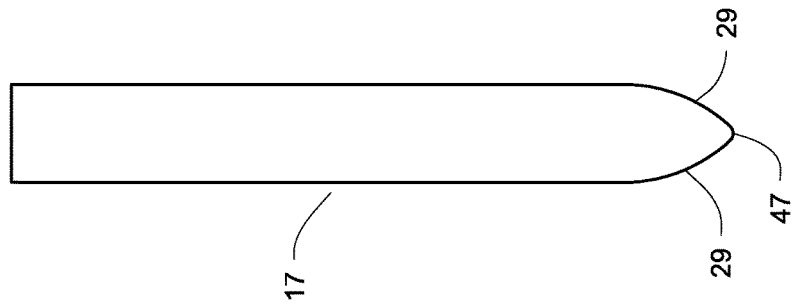
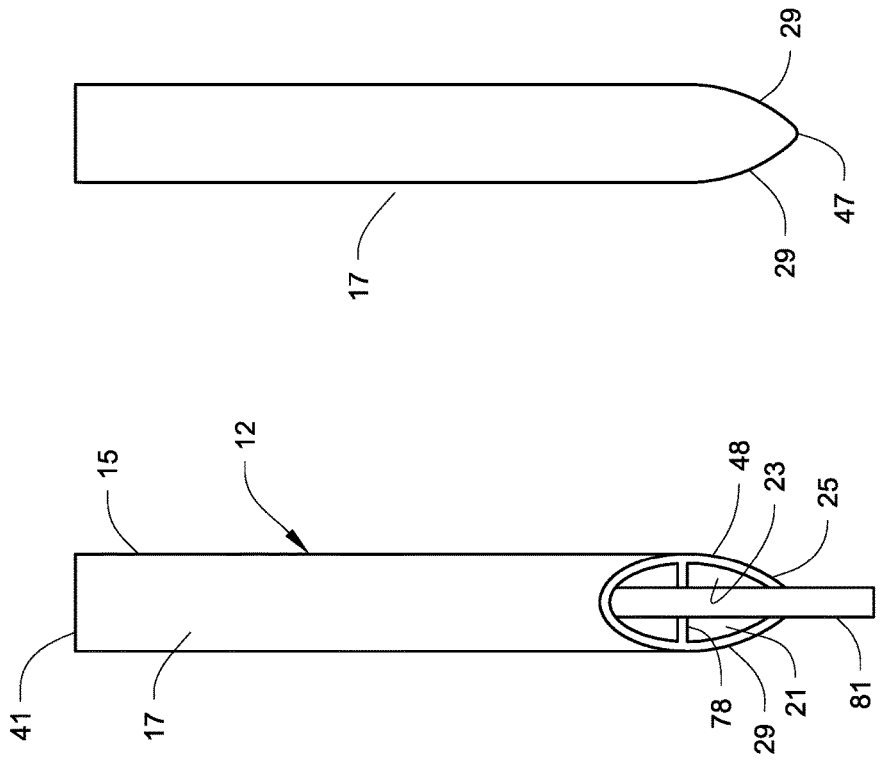
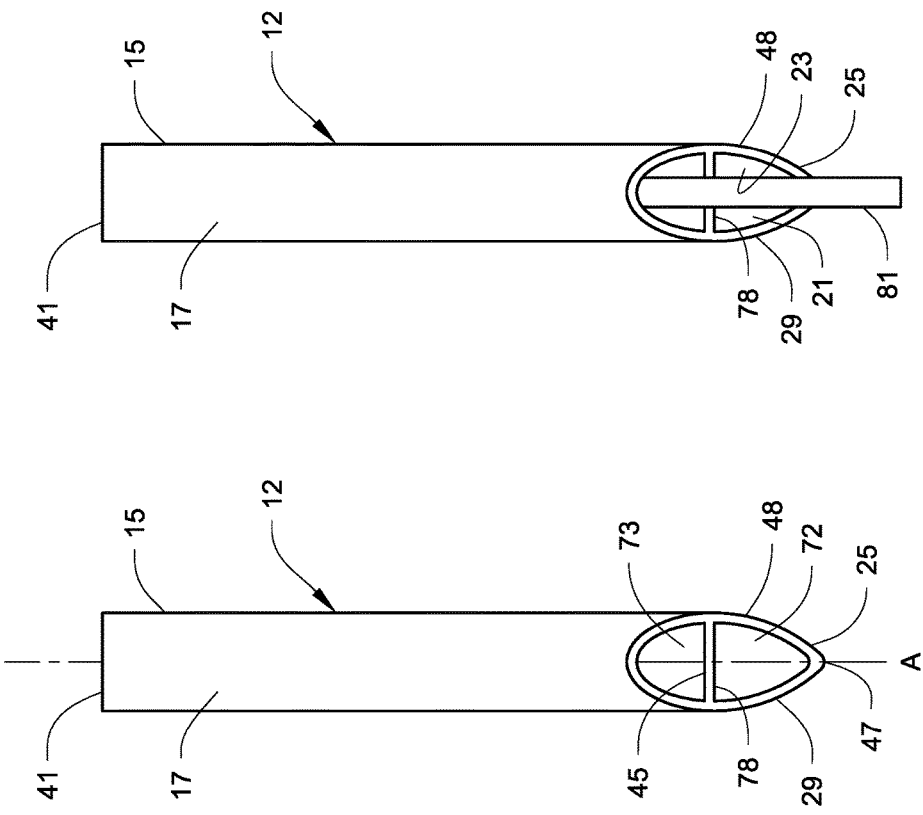

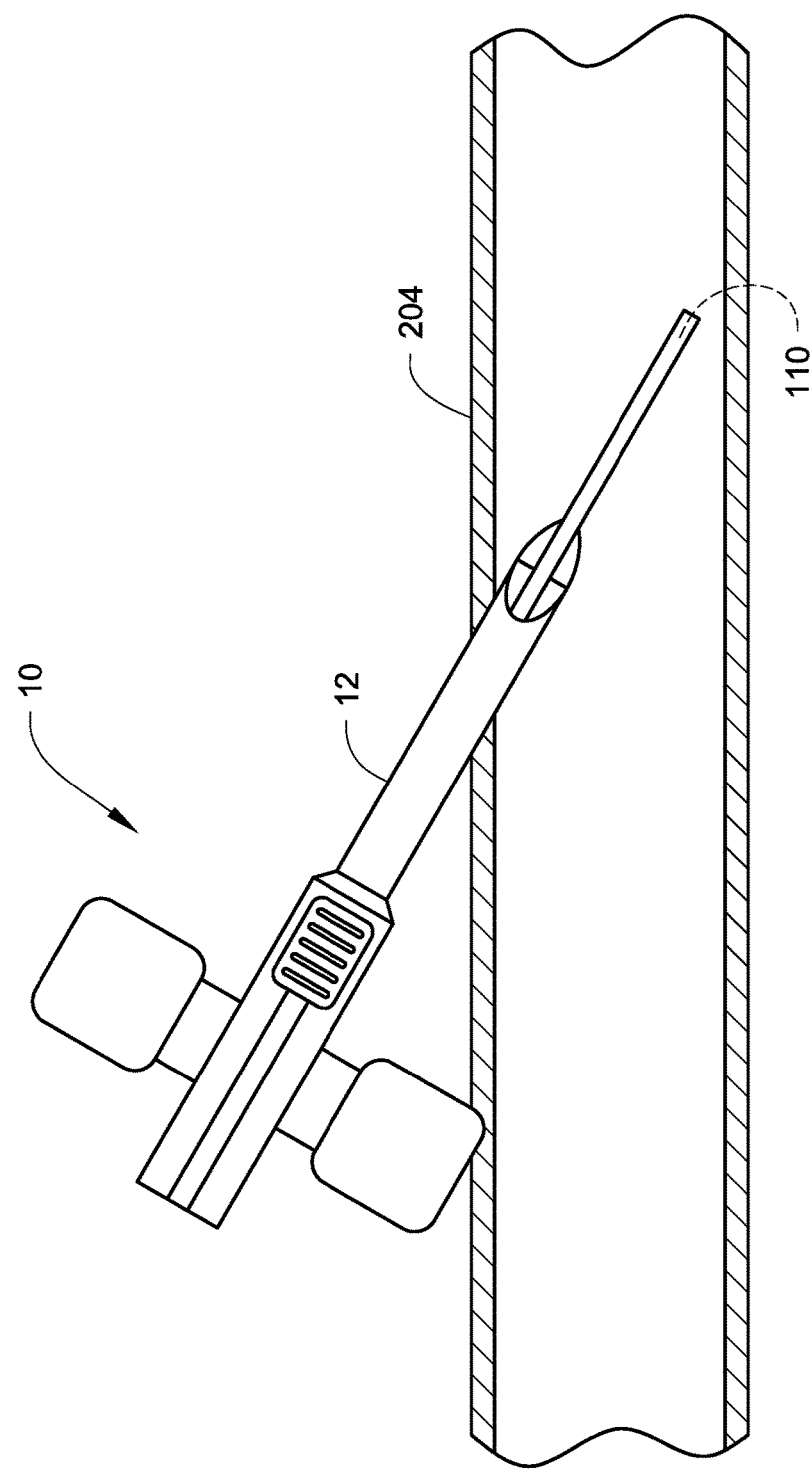

NEEDLE SYSTEM FOR MEDICAL USE

FIELD

The embodiments disclosed herein relate generally to a needle system for medical use and methods involving the use of the needle system. In particular, the needle system can be used to perform a hemodialysis on a patient at a single site.

BACKGROUND

Hemodialysis is a procedure where blood is withdrawn from the body into a machine that uses a dialyzer to filter wastes, and subsequently returned to the body in the filtered state so as to restore the electrolyte balance within the body. Hemodialysis can be performed using a single needle system or a double needle system. In general, insertion of a second needle is more difficult than that of the first needle and thus, using a single needle system is generally considered to ease some problems. However, the use of current single needle systems has many undesirable risk factors such as a higher risk of back filtration, blood recirculation and underdialysis.

SUMMARY

The embodiments described herein are directed to a needle system and methods for using the needle system. The needle system is generally intended for medical use. In some examples, the needle system can be used when performing a dialysis on a patient. In some examples, the dialysis can be hemodialysis. In general, the needle system described herein can address problems that commonly arise when using single or double needle systems during hemodialysis.

Generally, the disclosed needle system is configured for a single needle dialysis treatment. The term "single needle dialysis" means that a single puncture site is generally utilized for accessing a subject's blood circulation ("vascular access"), and is distinguishable from a "double-needle dialysis" in that the latter involves the use of at least two puncture sites for vascular access.

One drawback among others of the current single-needle dialysis system is blood recirculation. The term "blood recirculation" means a reflux of dialyzed blood of the venous line into the arterial line and the contamination the arterial blood by blood which has been already dialyzed, thus leading to a reduction in dialysis efficiency. The conventional method of dialysis via 2 needles placed at least 3 cm apart prevents the recirculation phenomenon. However, the double-needle approach is undesirable in that a longer segment of matured access is needed for the placement of both needles. This is not always readily available in patients. Also with double needle cannulation, there is increased wear of the access reducing its longevity. The needle system of the present disclosure is configured to address the problems that arise with conventional single and double needle dialysis systems while realizing the benefits of both approaches. Examples of conventional single-needle and double-needle dialysis systems are described in "Adequacy Studies of fistula single needle dialysis" in the American Journal of Kidney Disorder, December 1987; 10(6): 417-426 and NKF's 2006 KDOQI guidelines for double needle cannulation, Dialysis and Transplantation Vol. 24, No. 11, 1995, which is herein incorporated by reference.

In general, the needle system includes a needle and a tube that is provided within the needle. During use, the needle system generally is configured to be in a retracted state in which the tube is retracted within the needle, or in a protruded state in which the tube protrudes from the tip of the needle. In some examples, the needle system is used in a dialysis, and in this instance, the needle system is in a retracted state before obtaining intravenous access, and is in a protruded state after obtaining intravenous access.

In some examples, the needle system is configured so that when the vein is punctured with the needle to obtain intravenous access, the tube protrudes from the tip of the needle. In the retracted state, the tube is contained within the tube, while in the protruded state, the tube protrudes a predetermined distance from a tip of the needle. In some examples, the predetermined distance is a distance that is sufficient to reduce an incidence of recirculation of the blood as compared to that of where a conventional single needle dialysis is performed. In general, the needle system together with the tube is configured, e.g., in terms of the construction of the needle system, the material of the tube, dimensions of the tube and the distance of the protrusion, so that when the tube becomes subjected to a venous environment after the vein is punctured with the needle, the tube is capable of extending the predetermined distance, maintaining the extended state and performing the intended function of reducing an incidence of recirculation of the blood as compared to that of where a conventional single needle dialysis is performed.

In one embodiment, the needle system includes a needle that is a hollow shaft. In some examples, the hollow shaft has an exterior surface, an interior surface, an interior space and first and second ends that are in fluid communication with one another. In some examples, the first end is an open distal end and the second end is an open proximal end. In some examples, a blade is provided on the first end, where the opening is provided on the tip of the blade. In some examples, the second end is connected to an open end of a hub so that the second end of the needle is in fluid communication with the open end of the hub. In some examples, a winged guiding element is attached to a portion of the hub.

In some examples, the hollow shaft of the needle extends from the first end to the second end, thereby defining a longitudinal axis. In some examples, the needle includes a barrier. In some instances, the barrier is provided within the interior space of the hollow shaft and extends along the longitudinal axis as viewed in top cross-sectional view so that the interior wall of the hollow shaft and the barrier define first and second passageways that extend along the longitudinal axis of the hollow shaft. In some examples, the barrier extends along a chord of the hollow shaft as viewed in side cross-sectional view so that the interior wall of the hollow shaft and the barrier define first and second openings on the tip of the blade. In some examples, the needle system further includes a tube that can be provided in the first and/or second passageway. In some examples, the tube is provided in one of the passageways. In some instances, the tube is provided in the first passageway.

In some examples, the blade that is provided on the first end has a bias cut as viewed in cross-sectional view that defines a diagonal edge on the blade. The diagonal edge slopes from an upper diagonal end to a lower diagonal end, and converges with a bottom edge of the blade so that a needle sharp point of the blade is defined on the lower diagonal end. In some examples, the barrier extends along the longitudinal axis of the hollow shaft at about the midpoint of the diagonal edge so that the first passage is an upper passageway and the second passageway is a lower passageway.

In some examples, the upper passageway includes the tube. In some instances, the lower passageway is configured to receive blood from the artery while the tube in the protruded state is configured to return filtered blood to the vein.

In some examples, the needle system includes a sliding member that allows a user to switch from the retracted state to the protruded state. In some instances, the hub includes a slot on an upper wall that extends from a distal end to a proximal end along the longitudinal axis of the hub, and the sliding member is slidably mounted within the slot so as to allow sliding movement along the longitudinal axis of the slot. The sliding member is engaged with the tube so that when the sliding member is positioned on the distal end, the needle system is in the retracted state, and when a user slides the sliding member to the proximal end, the needle system is in the protruded state.

In one embodiment, the disclosed method involves the use of the needle system. In some examples, the needle system is used when dialysis is performed. In some examples, the dialysis that is performed is hemodialysis.

In some examples, the disclosed method generally involves obtaining intravenous access using the needle system, withdrawing blood from the subject, treating the withdrawn blood and returning the treated blood to the subject. In some instances, the needle system is in the retracted state when obtaining intravenous access, and in the protruded state when withdrawing and returning the blood to the subject. In some examples, the disclosed method involves the use of the needle system during dialysis so as to reduce an incidence of recirculation of the blood as compared to that of where conventional single needle dialysis is performed.

Other aspects of the invention will become apparent by consideration of the detailed description and accompanying drawings.

BRIEF DESCRIPTION OF THE DRAWINGS

FIGS. 3a and 3b illustrate cross-sectional side views of the retracted state and the protruded state, respectively, of the needle shown in FIG. 2.

FIGS. 4a and 4b illustrate a top plan view of a needle of the needle system shown in FIG. 2 in the retracted state and the protruded state, respectively. FIG. 4c shows a bottom view of the needle.

FIG. 6 illustrates a schematic view of the needle system shown in FIG. 2 being used during dialysis of a subject.

DETAILED DESCRIPTION

The embodiments described herein are directed to a needle system and methods for using the needle system. In general, the needle system can be used in a medical setting, and the description that follows will focus on the use of the needle system during hemodialysis in which the forearm provides venous access. However, it is to be realized that the concepts herein can apply in other types of medical settings, such as dialysis in which a portion of the body other than the forearm provides venous access. In some embodiments, the needle system can address problems that commonly arise when using conventional systems during hemodialysis such as recirculation.

Figure 1:
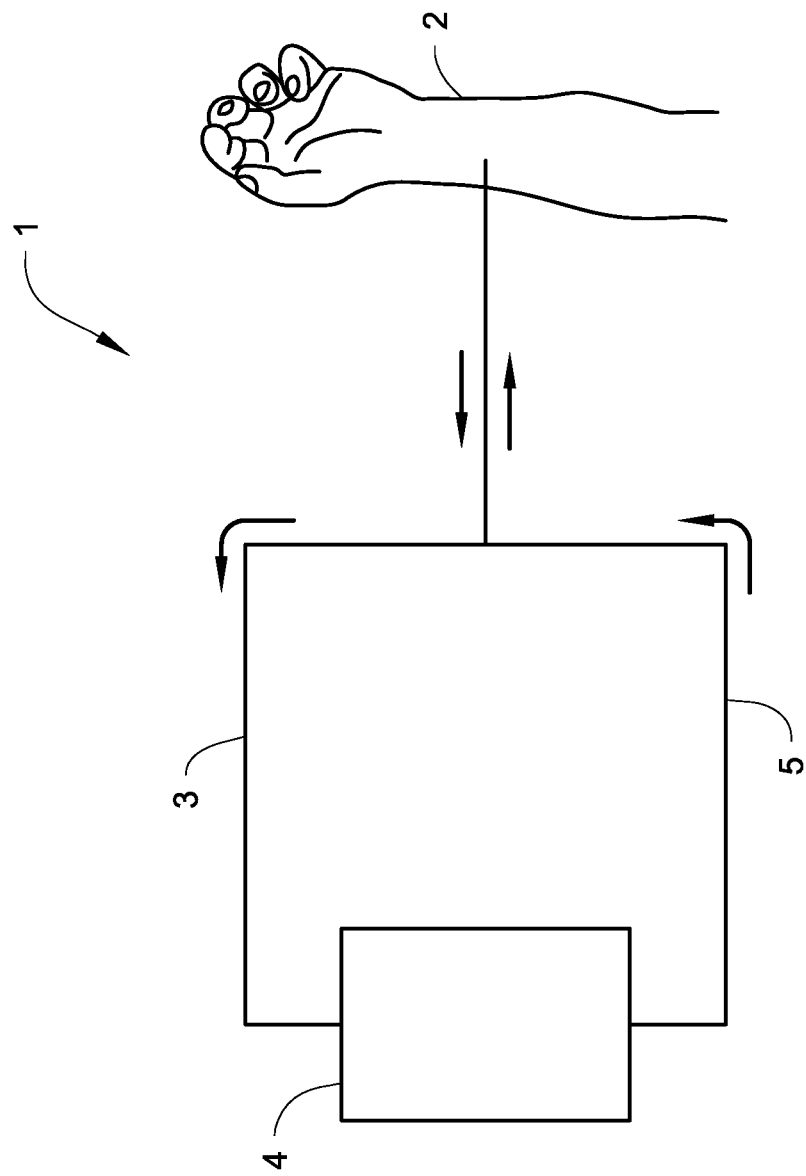
FIG. 1 illustrates a schematic view of a dialysis circuit utilizing a needle system including a needle, according to one embodiment.

FIG. 1 illustrates one example of a hemodialysis or external circuit 1 in which the disclosed needle system can be used. In this circuit 1, blood is withdrawn from an arm 2 of a patient and delivered via an arterial or receiving line 3 to a machine 4 that uses a dialyzer (not shown) to filter wastes, and subsequently returned to the arm 2 of the patient via the venous delivering line 5 in the filtered state so as to restore the electrolyte balance within the body of the patient.

Figure 2:
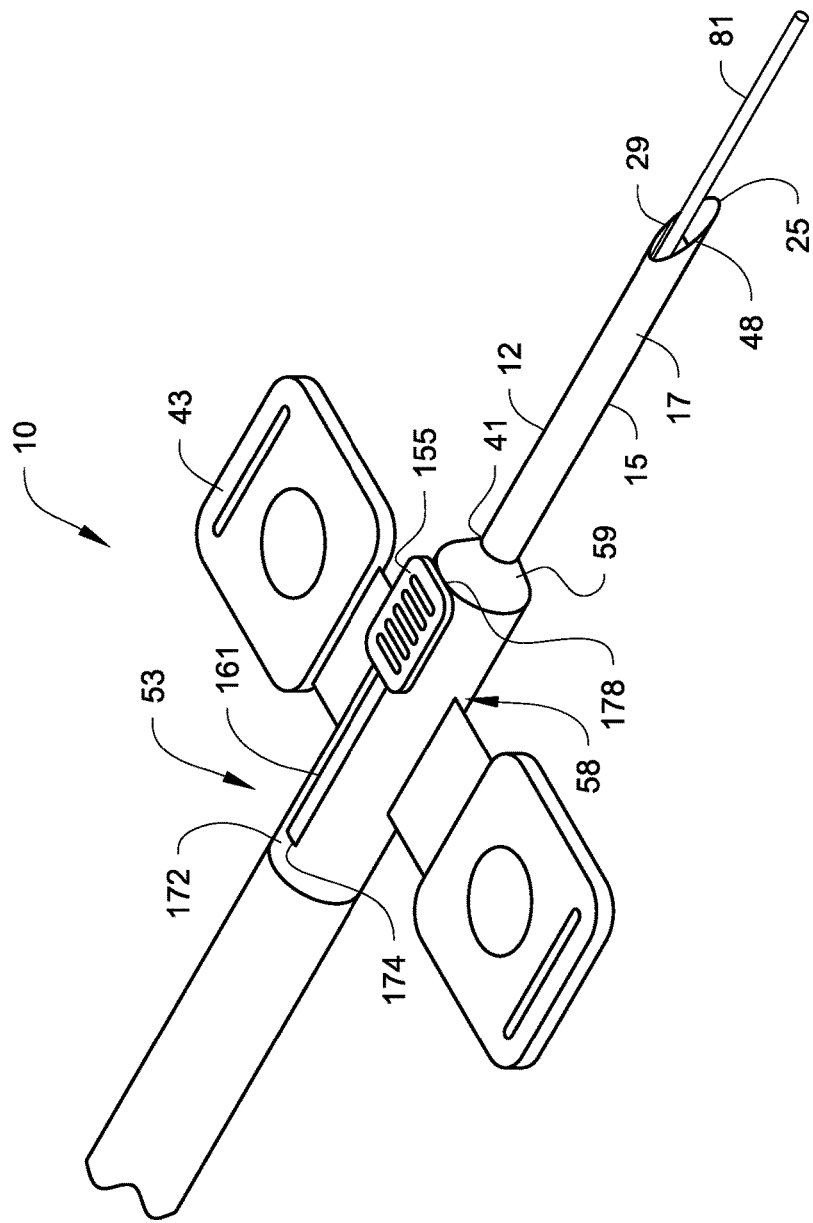
FIG. 2 illustrates a schematic view of a needle system including a needle, according to one embodiment.
Figure 5:
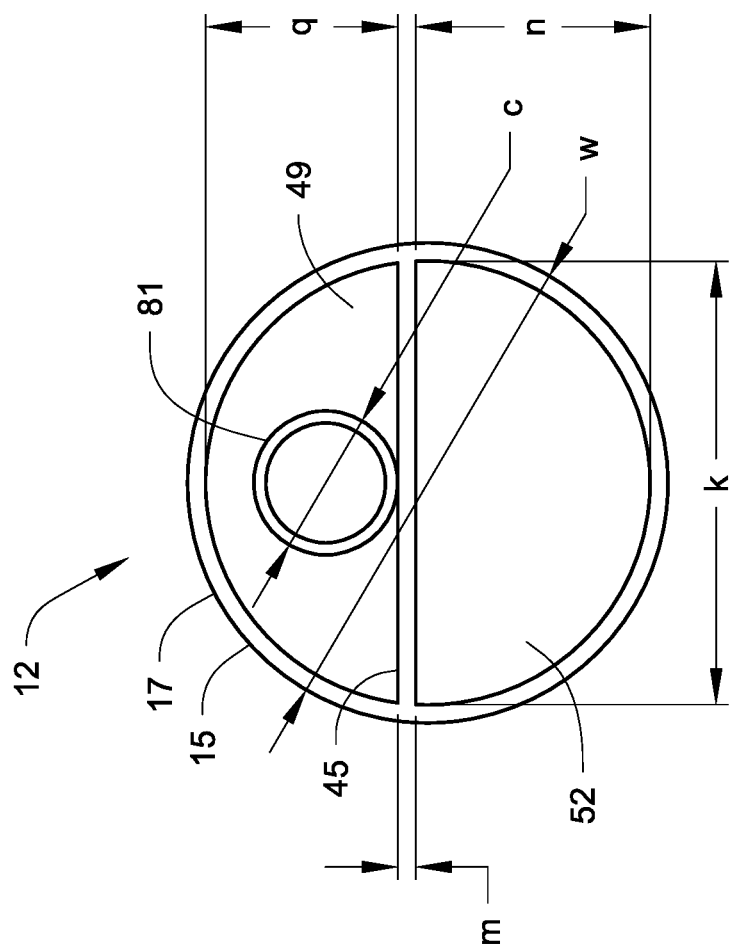
FIG. 5 illustrates a cross-sectional side view taken across an axis B-B of the needle shown in FIGS. 3a and 3b.

FIG. 2 shows a schematic view of one embodiment of a needle system 10 that includes a needle 12. FIGS. 3a and 3b show cross-sectional side views of the needle system 10, FIGS. 4a and 4b show top plan views of the needle 12 and FIG. 5 shows a cross-sectional view taken along line B-B of the needle 12 as shown in FIGS. 3a and 3b. In the description that follows, some of the advantages of the needle system 10 will be described as being realized during a single-needle dialysis treatment. However, it is to be realized that the use of the needle system 10 is not limited to a single-needle approach, and can be used in a double-needle dialysis treatment.

Referring to FIGS. 2, 3a, 3b, 4a and 4b, the needle 12 includes a hollow shaft 15. The hollow shaft 15 has an exterior surface 17, an interior surface 23 (see FIG. 4b) and an interior space 21 (see FIG. 4b). The hollow shaft 15 has first (proximal) and second (distal) ends 25, 41 that are in fluid communication with one another, and extends from the first end 25 to the second end 41, thereby defining a longitudinal axis A-A (see FIGS. 3a, 3b, 4a and 4b). The second end 41 of the needle 12 is connected to an open end 59 of a hub 53 so that the second end 41 of the needle 12 is in fluid communication with the open end 59 of the hub 53. The hub 53 is generally a hollow tube having an interior space 115 and has a diameter that is greater than that of the needle. The hub 53 extends from a third end 112 to a fourth end 114 along the longitudinal axis A-A (see FIG. 3a), where the open end 59 is provided on the third end 112 of the hub 53. A winged guiding element 43 is attached to a portion 58 of the hub 53.

The hollow shaft 15 is provided with a blade 48 on the first end 25. The blade 48 has a bias cut 32 as viewed in cross-sectional side view (see FIGS. 3a and 3b) that defines a diagonal edge 29 on the blade 48. The diagonal edge 29 is generally diagonal as viewed in cross-sectional side view and slopes from an upper diagonal end 118 to a lower diagonal end 120, and converges with a bottom edge 149 of the blade 48 so that a needle sharp point 47 of the blade is defined on the lower diagonal end 120.

In some examples, the needle system 10 includes a barrier 45. Referring to FIGS. 3a and 3b, the barrier 45 is provided within the interior space 21 of the hollow shaft 15 and extends along the longitudinal axis A-A as viewed in side cross-sectional view so that the interior wall 23 of the hollow shaft 15 and a surface of the barrier 45 define first and second passageways 49, 52 that extend along the longitudinal axis A-A of the hollow shaft 15. The first passageway 49 is provided on an upper side 64 of the needle 12 while the second passageway 52 is provided on a lower side 68 of the needle 12.

Referring to FIG. 5, the barrier 45 extends along a diameter 61 of the hollow shaft 15 as viewed in side cross-sectional view. Referring to FIGS. 4a and 4b, first and second openings 72, 73 are formed for the first and second passageways 49, 52, respectively at the first end 25 of the needle 12. The first and second openings 72, 73 are defined by the diagonal edges 29 of the blade 48 and an outer edge 78 of the barrier 45.

Referring to FIGS. 3a and 3b, the barrier 45 further extends from the second end 41 of the needle 12 to the fourth end 114 of the hub 53 along the longitudinal axis A-A, so that an interior wall 117 of the hub 53 and the surface of the barrier 45 define third and fourth passageways 125, 130 (a receiving passageway) that extend along the longitudinal axis A-A. The first passageway 49 of the needle 12 is in fluid communication with the third passageway 125 of the hub 53, while the second passageway 52 of the needle 12 is in fluid communication with the fourth passageway 130 of the hub 53 (the two together being a delivering passageway). In some examples, the barrier 45 continuously extends within the needle 12 and the hub 53 so as to provide fluid separation between the first and third passageways 45, 125 and the second and fourth passageways 52, 130.

Referring to FIGS. 3a and 3b, the needle system 10 further includes a tube 81 that is disposed within the first and third passageways 49, 125. The tube 81 is elongated along the longitudinal axis A-A and is generally dimensioned and configured so that it is movable within the passageways 49, 125 along the longitudinal axis A-A.

Referring to FIGS. 3a, 3b and 5, the needle 12 has a diameter w and a length f, the barrier 45 has a length k and a width m (not shown), the tube 81 has a diameter c (not shown) and the hub 53 has a length p. Further, the first passageway 49 has a height q and the second passageway 52 has a height n. In some examples, the length k can be in a range of about 1 mm to about 2 mm and the width m can be in the range of about 0.01 mm to about 0.1 mm. In some examples, the diameter w can be in a range of about 1 mm to about 2 mm. In some examples, the diameter c can be in a range of about 0.25 mm to about 0.75 mm. In some examples, the height q can be in a range of about 0.5 mm to about 0.8 mm and the height n can be in a range of about 0.9 mm to about 1.1 mm. In some examples the length p can be about 2 cm to about 4 cm. In some examples, the length f can be about 0.5 cm to about 2 cm. These numerical ranges are provided only for exemplary purposes, and it is to be realized that the dimensions of the needle 12, the barrier 45, the tube 81 and/or the first and second passageways 49, 52 can have any dimensions that are suitable for use in a dialysis treatment.

In some examples, the materials of the needle 12, the tube 81 and the barrier 45 can be any material that is suitable for use during dialysis. In some examples, the material of the needle 12 and the barrier 45 can be metal, for example, stainless steel. In some examples, the tube 81 can be made of a polymer, e.g. plastic polymer.

In some embodiments, the needle system 10 is configured so that it can be adjusted from a retracted state (a first configuration) to a protruded state (a second configuration) where each of these states is defined by the position of the tube 81. FIGS. 3a and 4a show one example of the needle system 10 being in the retracted state, while FIGS. 1, 3b and 4b show one example of the needle system 10 being in a protruded state.

Referring to FIGS. 3a and 4a, in the retracted state, the tube 81 is retracted within the needle 12 so that a tip portion 91 of the tube 81 is generally not exposed and does not extend beyond the edge 29 of the blade 25. Referring to FIGS. 1, 3b and 4b, in the protruded state, the tube 81 extends a predetermined distance X from the edge 29 of the blade 25.

FIG. 6 illustrates the needle system 10 being used in a single needle dialysis where the needle 12 is punctured into a vein 204 of the subject. In the instance where the needle system 10 is used in the single needle dialysis, the needle system 10 is in the retracted state before obtaining intravenous access, that is, before the needle 12 is punctured into the vein 204 of the subject. In some examples, the needle system 10 is in the protruded state after obtaining intravenous access, that is, after the needle 12 is punctured into the vein 204 of the subject. In some examples of the protruded state, the tube 81 extends a predetermined distance X (see FIG. 3b) from the edge 29 of the blade 25. In some examples, the predetermined distance X is a distance sufficient to reduce an incidence of recirculation as compared to that of when a conventional single-needle dialysis is performed. In some examples, the predetermined distance X is about 2 cm to about 4 cm. In some examples, the predetermined distance X is about 3 cm.

In some examples of the protruded state, the opening 72 of the second passageway 52 is configured to receive blood from an artery (not shown), while the tube 81 that protrudes a predetermined distance is configured to return filtered blood to the vein 204 through an opening 110 of the tube 81. In some examples, the second passageway 52 and the tube 81 are configured to receive and return blood, respectively, at a rate that is sufficient for conducting a dialysis. In some examples, the rate can be between about 300 to about 400 mL/min.

The mechanism that is utilized to move the tube 81 within the passageway 49 will now be described. Referring to FIGS. 2, 3a and 3b, the needle system 10 includes a sliding member 155 moveably attached to the hub that allows a user to switch from the retracted state to the protruded state by sliding the sliding member 155 along the longitudinal axis A-A of the hub 53 using, for example, his/her own thumb. The sliding member 155 includes a thumb bar 182 and a flange 196 that extends downwardly from the thumb bar 182. The hub 53 includes a slot 161 on an upper wall 172 that extends from a distal end 174 to a proximal end 178 along the longitudinal axis A-A of the hub 53, and the sliding member 155 is slidably mounted within the slot 161 so that the flange 196 is fitted into the slot 161 and allows sliding movement of the sliding member 155 along the longitudinal axis A-A. The flange 196 of the sliding member 155 is fixedly attached with the tube 81 so that when the sliding member 155 is positioned on the distal end 174, the needle system 10 is in the retracted state, and when a user slides the sliding member 155 to the proximal end 178, the needle system 10 is in the protruded state. The hub 53 also includes a lock 202 so that when a user slides the sliding member 155 to the proximal end 178, the lock 202 secures the position of the sliding member 155 at the proximal end so as to lock the needle system 10 in the protruded state. With the tube in the protruded state, the system in combination with the external circuit is operable.

In the embodiments described above, the tube 81 is shown to be provided in the upper passageway 49 of the needle 12. However, it is to be realized that the tube 81 may be provided in the lower passageway 52 of the needle 12.

In one embodiment, the disclosed method involves the use of the needle system 10. In some examples, the needle system 10 is used when dialysis is performed. In some examples, the dialysis that is performed is hemodialysis.

In some examples, the disclosed method generally involves obtaining intravenous access using the needle system 10, withdrawing blood from the subject, treating the withdrawn blood and returning the treated blood to the subject. In some instances, the needle system 10 is in the retracted state when obtaining intravenous access, and in the protruded state when withdrawing and returning the blood to the subject. In some examples, the disclosed method involves the use of the needle system 10 during dialysis so as to reduce an incidence of recirculation of the blood as compared to that of where conventional single needle dialysis is performed.

With regard to the foregoing description, it is to be understood that changes may be made in detail, especially in matters of the construction materials employed and the shape, size and arrangement of the parts without departing from the scope of the present invention. It is intended that the specification and depicted embodiment to be considered exemplary only, with a true scope and spirit of the invention being indicated by the broad meaning of the claims.

What is claimed is:

1. A needle system attached to an external circuit having a receiving line and a delivering line, comprising:
   a needle and a hub connected to one another and configured to form a receiving passageway and a delivering passageway in fluid communication with the receiving line and the delivering line of the external circuit, respectively; and
   a tube and a sliding member fixedly attached to one another and movable between a first configuration wherein said tube is fully within said needle and said hub, and a second configuration wherein said tube extends outward from said needle, said sliding member being movably attached to said hub, wherein said needle system in said first configuration may be installed in a patient and is operable relative to said patient in said second configuration,
   wherein the needle includes a hollow shaft, wherein the hollow shaft has an exterior surface and an interior surface, wherein the hollow shaft has first and second ends that are in fluid communication with one another, wherein the hollow shaft extends from the first end to the second end, thereby defining a longitudinal axis, wherein the second end is connected to an open end of the hub, the hub being a hollow tube having an interior space and has a diameter that is greater than that of the needle,
   wherein a barrier is provided within the interior space of the hollow shaft of the needle and extends along the longitudinal axis as viewed in side cross-sectional view of the interior wall of the hollow shaft, wherein a surface of the barrier defines first and second passageways that extend along the longitudinal axis of the hollow shaft,
   wherein the hollow shaft is provided with a blade on the first end, and
   wherein the blade has a bias cut as viewed in cross-sectional side view that defines a diagonal edge on the blade, the diagonal edge is diagonal as viewed in cross-sectional side view and slopes from an upper diagonal end to a lower diagonal end, and converges with a bottom edge of the blade so that a needle sharp point of the blade is defined on the lower diagonal end, and first and second openings are defined by the diagonal edges of the blade and an outer edge of the barrier.

2. The needle system in accordance with claim 1 wherein said sliding member includes a locking mechanism.

3. The needle system in accordance with claim 1, wherein the barrier extends along a diameter of the hollow shaft as viewed in side-cross-sectional view.

4. The needle system in accordance with claim 1, wherein first and second openings are formed for the first and second passageways, respectively, at the first end of the hollow shaft.

5. The needle system in accordance with claim 1, wherein the first passageway is provided on an upper side of the needle and the second passageway is provided on the lower side of the needle.

6. The needle system in accordance with claim 5, wherein the tube is disposed within the first passageway.

7. A needle system for receiving first blood from and delivering second blood to a vein of a patient, said needle system being attached to an external circuit having a receiving line and a delivering line, comprising:
   a needle that includes a hollow shaft, the hollow shaft has a first interior defined by an exterior surface and an interior surface, the first interior includes a first barrier separating the first interior into first and second passageways;
   a hub having a second interior with a second barrier separating the second interior into third and fourth passageways, said first and third passageways in fluid communication with said receiving line and said fourth passageway in fluid communication with said delivering line, said hub having a slot;
   wherein the hollow shaft of the needle has first and second ends that are in fluid communication with one another, wherein the hollow shaft extends from the first end to the second end, thereby defining a longitudinal axis, wherein the second end is connected to an open end of the hub, the hub being a hollow tube defined by the second interior and has a diameter that is greater than that of the needle,
   wherein the first barrier extends along the longitudinal axis as viewed in side cross-sectional view of the interior wall of the hollow shaft, wherein the first and second passageways extend along the longitudinal axis of the hollow shaft and a surface of the first barrier defines the first and second passageways,
   a tube positioned within said second and fourth passageways, said tube in fluid communication with said fourth passageway; and
   a sliding member fixedly attached to said tube and slideably attached to said hub, said sliding member extending through the slot in said hub;
   wherein in a first configuration, said sliding member is at a distal end of the slot in said hub and said tube is fully within said second and fourth passageways, and wherein in a second configuration, said sliding member is at a proximal end of the slot in said hub and a portion of said tube extends out of the second passageway of said needle,
   wherein the hollow shaft is provided with a blade on the first end, and
   wherein the blade has a bias cut as viewed in cross-sectional side view that defines a diagonal edge on the blade, the diagonal edge is diagonal as viewed in cross-sectional side view and slopes from an upper diagonal end to a lower diagonal end, and converges with a bottom edge of the blade so that a needle sharp point of the blade is defined on the lower diagonal end, and first and second openings are defined by the diagonal edges of the blade and an outer edge of the barrier.

8. A method of using a needle system attached to an external circuit having a receiving line and a delivering line, said needle system including a needle and a hub connected to one another and configured to form a receiving passageway and a delivering passageway in fluid communication with the receiving line and the delivering line of the external circuit, respectively, wherein the needle includes a hollow shaft, wherein the hollow shaft has an exterior surface and an interior surface, wherein the hollow shaft has first and second ends that are in fluid communication with one another, wherein the hollow shaft extends from the first end to the second end, thereby defining a longitudinal axis, wherein the second end is connected to an open end of the hub, the hub being a hollow tube having an interior space and has a diameter that is greater than that of the needle, wherein a barrier is provided within the interior space of the hollow shaft of the needle and extends along the longitudinal axis as viewed in side cross-sectional view of the interior wall of the hollow shaft, wherein a surface of the barrier defines first and second passageways that extend along the longitudinal axis of the hollow shaft, the hollow shaft is provided with a blade on the first end, wherein the blade has a bias cut as viewed in cross-sectional side view that defines a diagonal edge on the blade, the diagonal edge is diagonal as viewed in cross-sectional side view and slopes from an upper diagonal end to a lower diagonal end, and converges with a bottom edge of the blade so that a needle sharp point of the blade is defined on the lower diagonal end, and first and second openings are defined by the diagonal edges of the blade and an outer edge of the barrier, said needle system further including a tube and a sliding member fixedly attached to one another and movable between a first configuration wherein said tube is fully within said needle and said hub, and a second configuration wherein said tube extends outward from said needle, said sliding member being movably attached to said hub, said method comprising:

using said blade of said needle to insert said needle into a vein of a patient;

using said sliding member to move said needle system between the first and second configurations; and operating said external circuit in combination with said needle system.

\* \* \* \* \*